(12) United States Patent
Hasegawa et al.

(10) Patent No.: US 7,771,928 B2
(45) Date of Patent: Aug. 10, 2010

(54) IMMUNOASSAY DEVICE AND IMMUNOASSAY METHOD USING THE SAME

(75) Inventors: Akira Hasegawa, Tokyo (JP); Yoshihiro Ashihara, Tokyo (JP); Mitsuo Isomura, Tokyo (JP)

(73) Assignee: Fujirebio Inc., Tokyo (JP)

( * ) Notice: Subject to any disclaimer, the term of this patent is extended or adjusted under 35 U.S.C. 154(b) by 1040 days.

(21) Appl. No.: 10/229,020

(22) Filed: Aug. 28, 2002

(65) Prior Publication Data

US 2003/0100103 A1 May 29, 2003

Related U.S. Application Data

(60) Division of application No. 09/492,191, filed on Jan. 27, 2000, now Pat. No. 6,472,160, which is a continuation-in-part of application No. 08/706,686, filed on Sep. 6, 1996, now abandoned.

(30) Foreign Application Priority Data

| Sep. 8, 1995 | (JP) | ................................... 7-256756 |
| Sep. 8, 1995 | (JP) | ................................... 7-256757 |
| Dec. 20, 1995 | (JP) | ................................... 7-348528 |

(51) Int. Cl.
*G01N 33/53* (2006.01)

(52) U.S. Cl. ........................ 435/5; 435/7.1; 435/7.35; 435/962; 435/970; 435/975; 436/514; 436/518; 436/501; 436/523; 436/524; 436/525; 436/530; 436/541; 436/810; 436/814; 436/817; 436/818; 436/906

(58) Field of Classification Search ................. 436/518, 436/523, 528–531, 823, 514, 501, 524, 525, 436/541, 810, 814, 817, 818, 906, 962; 435/7.1, 435/7.9, 7.94, 287.7, 287.9, 970, 7.36, 962, 435/975, 7.35

See application file for complete search history.

(56) References Cited

U.S. PATENT DOCUMENTS

| 4,094,647 A | 6/1978 | Deutsch et al. |
| 4,416,813 A | 11/1983 | Ikeda et al. |
| 4,857,453 A | 8/1989 | Ullman et al. |
| 4,861,711 A | 8/1989 | Friesen et al. |
| 4,981,786 A | 1/1991 | Dafforn et al. |
| 5,075,078 A | 12/1991 | Osikowicz et al. |

(Continued)

FOREIGN PATENT DOCUMENTS

EP 0 323 605 7/1989

(Continued)

OTHER PUBLICATIONS

K. Ishikawa, et al., Igaku To Yakugaku (Medial and Pharmaceutical Sciences), vol. 32, No. 6, pp. 1301-1305, Dec. 1994 (with partial English translation).

(Continued)

*Primary Examiner*—Bao-Thuy L Nguyen
(74) *Attorney, Agent, or Firm*—Oblon, Spivak, McClelland, Maier & Neustadt, L.L.P.

(57) ABSTRACT

Disclosed are an immunoassay device which comprises a labeled substance dotting portion and a specimen dotting portion provided thereon, and an immunoassay method using the device.

17 Claims, 5 Drawing Sheets

Solution Transferring Direction of a Developing Solution

U.S. PATENT DOCUMENTS

| | | | |
|---|---|---|---|
| 5,217,905 A * | 6/1993 | Marchand et al. | 436/518 |
| 5,500,350 A | 3/1996 | Baker et al. | |
| 5,602,040 A * | 2/1997 | May et al. | 436/514 |
| 5,753,459 A * | 5/1998 | Blanco et al. | 435/69.1 |
| 6,017,494 A | 1/2000 | Ashihara et al. | |

FOREIGN PATENT DOCUMENTS

| | | |
|---|---|---|
| EP | 0 462 376 | 12/1991 |
| EP | 0 585 912 | 3/1994 |
| EP | 0 762123 | 3/1997 |
| EP | 0762123 A1 * | 12/1997 |
| JP | 06-174711 | 6/1994 |
| WO | WO 88/08534 * | 11/1988 |

OTHER PUBLICATIONS

Dinabbott Co. Ltd.. "Instruction Manual of Dainascreen AUSAB, A Kit for Detecting and Measuring HBs Antibody in Blood Using Immunochromatography Assay", Aug. 1994 (with partial English translation).

S. Kashiwagi, et al., Kansen-sho Gaku Zasshi (Journal of the Study on Infective Diseases), vol. 69, No. 3, pp. 297-302, "Immunochromatography Assay". Mar. 20, 1995 (with English Abstract).

L. M. Weigel, et al., Infection and Immunity, vol. 60, No. 4, pp. 1568-1576, "Analysis of the N-Terminal Region of the 47-Kilodalton Integral Membrane Lipoprotein of Treponema Pallidum", Apr. 1992 (with English translation).

M. Zrein, et al., Journal of Clinical Microbiology, vol. 33, No. 3. pp. 525-527, "Recombinant Antigen-Based Enzyme Immunoassay for Screening of Treponema Pallidum Antibodies in Blood Bank Routine", Mar. 1995 (with English translation).

* cited by examiner

Solution Transferring Direction
of a Developing Solution

Solution Transferring Direction
of a Developing Solution

Solution Transferring Direction
of a Developing Solution

Solution Transferring Direction
of a Developing Solution

Solution Transferring Direction
of a Developing Solution

Solution Transferring Direction
of a Developing Solution

Solution Transferring Direction of a Developing Solution

Solution Transferring Direction of a Developing Solution

IMMUNOASSAY DEVICE AND IMMUNOASSAY METHOD USING THE SAME

This application is a Continuation of U.S. application Ser. No. 09/492,191, filed on Jan. 27, 2000, now allowed, which is a Continuation-in-Part of U.S. application Ser. No. 08/706,686, filed Sep. 6, 1996, now abandoned.

BACKGROUND OF THE INVENTION

This invention relates to an immunoassay device to be used for detecting an antigen or antibody in a specimen, and an immunoassay method using the same.

This invention also relates to an immunoassay method which comprises adding a specimen to an immunoassay device in which a labeling reagent zone comprising a labeled genetic recombinant syphilis treponeme (*Treponema pallidum*, hereinafter referred to as "TP") antigen and a detection zone in which a TP antigen is immobilized to a matrix which can transfer a solution by capillarity are provided on the matrix; and detecting an anti-syphilis treponeme antibody (hereinafter referred to as "the anti-TP antibody") in the specimen which is bound to the detection zone, and an immunoassay device to be used for said assay.

As a device which detects an antigen or antibody in a specimen simply and easily, an immunoassay device has been used. A conventional immunoassay device is schematically shown in FIG. 11 (see Japanese Provisional Patent Publication No. 47894/1978). The conventional immunoassay device has a membrane portion 20 comprising a material such as cellulose, and a developing solution-supplying portion 22 and an absorption portion 24 each comprising a water-absorbable material, provided at both ends of the membrane portion 20, respectively. In the membrane portion 20, a labeled substance dotting portion 26 to which a labeled substance labeled with a radioisotope is dotted is provided. Further, a detection line 28 is provided between the labeled substance dotting portion 26 and the absorption portion 24. At the detection line 28, an antibody or antigen which reacts with an antigen or antibody to be detected is immobilized to a membrane. Further, between the labeled substance dotting portion 26 and the developing solution-supplying portion 22, a specimen dotting portion 29 is provided.

When the device is used, a specimen solution is added to the specimen dotting portion 29, and a developing solution is added to the developing solution-supplying portion 22. The developing solution is developed from the developing solution-supplying portion 22 and reaches to the specimen dotting portion 29. The specimen dotted to the specimen dotting portion 29 is flowed by the developing solution flowing from the developing solution-supplying portion 22, reaches to the labeled substance dotting portion 26 and reacts with the labeled substance. When the reaction mixture is further flowed by the developing solution and reaches to the detection line 28, an antigen or antibody in the specimen is trapped by an antibody or antigen immobilized to the detection line 28 and held there. In this case, the antigen or antibody in the specimen is bound to the labeled substance so that the labeled substance is also held at the detection line 28. Therefore, when the antigen or antibody to be detected is contained in the specimen solution, the signal of the radioisotope is observed on the detection line 28. The developing solution and other components which are not trapped are absorbed into the absorption portion 24. On the other hand, when the antigen or antibody to be detected is not contained in the specimen solution, the labeled substance is not trapped at the detection line 28 and therefore is absorbed as such into the absorption portion 24, whereby the signal is not observed on the detection line 28. Thus, whether or not the antigen or antibody to be detected is contained in the specimen can be found by whether or not the signal of the radioisotope is detected at the detection line 28.

However, in the conventional immunoassay device as described above, there are problems that since the specimen dotted to the specimen dotting portion 29 is diluted with the developing solution during measurement, lowering of detection sensitivity is caused, and since the labeled substance is dissolved in the developing solution during development and reacts with the specimen, when an object to be measured has low concentration, in order to carry out an accurate test, a long reaction time is required to be taken.

An immunoassay device using a color latex has been also known. In this device, color latex particles to which an antibody or antigen which reacts with an antigen or antibody to be detected is bound are used as a labeled substance. This device is schematically shown in FIG. 4. A labeled substance dotting portion 32 is provided at one end of a membrane portion 30, and the above labeled substance is contained in the labeled substance dotting portion 32. On the other hand, to a detection line 36 is immobilized an antibody or antigen which reacts with an antigen or antibody to be detected. A specimen solution is added to a sample dotting portion 34 in the labeled substance dotting portion 32. The specimen solution and the labeled substance dissolved by the specimen solution are flowed while they are reacted, and when an antigen or antibody to be detected is contained in the specimen solution, the labeled substance is trapped at the detection line 36 as in the above case. The labeled substance contains a color latex so that the detection line 36 is colored. On the other hand, when the antigen or antibody to be detected is not contained in the specimen solution, the labeled substance is not trapped at the detection line 36 so that the detection line 36 is not colored. Thus, whether or not the antigen or antibody to be detected is contained in the specimen solution can be found by whether or not the detection line 36 is colored.

However, in the conventional immunoassay devices, there is a problem that a result which was negative at the time of judgment may be changed to be positive with a lapse of time. Therefore, when plural specimens are judged under the same conditions, it is necessary to carry out judgment at a certain judgment time or carry out judgment after a reaction is terminated by adding a reaction-terminating solution after a lapse of a certain period of time. However, when a large number of specimens are tested in parallel as in clinical tests, it is difficult to carry out judgment of all specimens at the same judgment time or add a reaction-terminating solution after a lapse of the same period of time. Further, when a reaction-terminating solution is added, the number of steps is increased to make an operation troublesome.

It is important to analyze living body components or drugs contained in blood, urine and the like for diagnosis of conditions of diseases and judgment of progress after therapy. As a method for analyzing these living body components, drugs and the like from a specimen simply and easily by utilizing an antigen-antibody reaction, there has been found a method of using a strip assay device comprising a strip-shaped filter paper impregnated with a reaction reagent. This assay method is a method in which a specimen is added to a specimen dotting zone provided on the filter paper of the device, a solution is developed and diagnosis is carried out from the degree of coloring shown at a detection zone provided on the filter paper. In the above strip assay device, a filter paper containing a necessary reagent (an enzyme-labeled antibody, a substrate, a coloring reagent or the like) depending on the system of a reaction is used, and analysis is carried out from coloring thereof so that a simple and easy method can be carried out without using a special judgment device. Also, there has been known an assay method of using a color latex or particles of metal colloid or the like as a labeled substance. In this assay method, analysis is carried out by using a reagent in which an antibody or antigen which reacts with an antigen or antibody to be detected is bound to particles and detecting the image of the particles bound to a detection zone.

In the prior art, as a method for detecting the anti-TP antibody, there have been known a method of using a TPHA reagent in which a TP cell component is bound to hemocytes, a method of using an indirect agglutination immunoassay reagent produced by binding a TP antigen to artificial particles and a method of using an immunoassay reagent comprising a TP antigen-binding solid phase and a labeled antiglobulin antibody. In all of these methods, 2 hours or longer is required from starting measurement to obtaining a result, and a measurement apparatus is used for judgment so that the methods cannot be used for an emergency test and measurement at a bedside within a short period of time.

In a method for measuring the anti-TP antibody using a conventional strip assay device, a reaction occurs between large amounts of globulin and a labeled antibody existing in a specimen, whereby measurement cannot be carried out. Therefore, there have been found a method of using a device in which a washing reservoir is added to an assay device (Japanese Provisional Patent Publication No. 126832/1993) and a method of using a device in which a zone for preventing signals generated by a labeled substance is provided in a developing solution (PCT Provisional Patent Publication No. 503439/1989).

In these methods, operations are complicated, and it is difficult to carry out measurement operations under constant conditions at all times. Further, due to influence of globulin or the like contained in a specimen, the methods are not satisfactory for carrying out measurement with good sensitivity. In order to solve such problems, when measurement of the anti-TP antibody in a specimen is carried out, it has been attempted to detect said antibody by using a TP antigen and a labeled TP antigen bound to a solid phase according to the sandwich method. However, it was not easy to introduce a labeled substance into a mixture containing a TP antigen obtained by culturing in a living body in the prior art, and a labeled antigen reagent which was substituted by a constant labeled substance at all times could not be obtained continuously. As described above, a method of using a labeled TP antigen has not been known.

In a conventional measurement method for the anti-TP antibody, there are problems that an operation is complicated and analysis with high precision cannot be carried out within a short period of time.

SUMMARY OF THE INVENTION

A first object of the present invention is to provide an immunoassay device in which detection sensitivity is high and an accurate test can be carried out within a shorter period of time as compared with a conventional immunoassay device, and an immunoassay method using the same.

A second object of the present invention is to provide an immunoassay device in which a judgment result which was negative at the time of judgment is not changed to be positive with a lapse of time, and an immunoassay method using the same.

A third object of the present invention is to provide an assay method by which a result can be obtained within a short period of time by a simple and easy operation as compared with a conventional method, and a device for practicing said assay.

The present inventors have studied intensively and consequently found that low sensitivity of a conventional assay device is caused by problems that a specimen dotted to a specimen dotting portion is diluted before it reacts with a labeled substance, a reaction of a labeled substance dotted to a labeled substance dotting portion and a specimen dotted to a specimen dotting portion is not carried out sufficiently, and the amount of a specimen solution dotted to a specimen dotting portion is small, and further found that these problems can be solved by incorporating a labeled substance on a membrane, to accomplish the present invention.

That is, the present invention provides an immunoassay device which comprises a labeled substance dotting portion and a specimen dotting portion provided thereon.

Also, the present inventors have studied intensively and consequently found that the above second object can be achieved not by incorporating a substrate of an enzyme into a developing solution as in the prior art, but by incorporating a substrate of an enzyme into a membrane in a dry state, to accomplish the present invention.

That is, the present invention provides an immunoassay device, comprising: a membrane portion; a labeled substance dotting portion provided on the membrane portion, wherein the labeled substance dotting portion comprises a pad of an absorbable material which contains a labeled substance and wherein the labeled substance is in mobilizable/diffusively bound form in the pad; a specimen dotting portion provided on the labeled substance dotting portion; a developing solution-supplying portion having a breakable solution reservoir, wherein the breakable solution reservoir contains a developing solution; a water-absorbable pad, wherein the developing solution-supplying portion and the water-absorbable pad are at opposite ends of the membrane portion; and a detection portion provided between the labeled substance dotting portion and the water absorbable pad, wherein an antibody or antigen is immobilized in the detection portion; wherein the labeled substance dotting portion is provided between the detection portion and the developing solution-supplying portion and yet at a position where a ratio LX/LT is less than 0.5, wherein LX is the distance from the longitudinal center of said labeled substance dotting portion to an end of said water-absorbable pad, the end of which is present at an upstream side of the solution transferring direction of the developing solution, and LT is the distance from said end of said water-absorbable pad to an end of said developing solution-supplying portion, the end of which is present at a downstream side of the solution transferring direction of the developing solution. Further, the present invention provides an immunoassay method using the above assay device of the present invention.

The present inventors have studied intensively and consequently found an immunoassay method in which a specimen is added to an immunoassay device for an anti-syphilis treponeme antibody, in which a labeling reagent zone comprising a labeled genetic recombinant TP antigen and a detection zone in which a TP antigen is immobilized to a matrix which can transfer a solution by capillarity are provided on the matrix; and an anti-syphilis treponeme antibody in the specimen bound to the detection zone is detected, and a novel immunoassay device for the anti-TP antibody, in which a labeling reagent zone comprising a labeled genetic recombinant TP antigen is provided on a matrix which can transfer a solution by capillarity, to accomplish the present invention. More specifically, they have found an immunoassay method which comprises using an immunoassay device for the anti- TP antibody, in which a developing solution zone containing a substrate, a labeling reagent zone comprising a genetic recombinant TP antigen labeled with an enzyme, a detection zone in which a TP antigen is immobilized to a matrix which can transfer a solution by capillarity, a specimen dotting zone and a developing solution-absorbing zone are provided on the matrix; dotting a specimen solution to the specimen dotting zone; supplying a developing solution to the developing solution zone; and detecting the enzyme immobilized to the detection zone in an amount depending on the anti-TP antibody in the specimen solution, with the substrate, and an immunoassay method which comprises using an immunoassay device for the anti-TP antibody, in which a specimen developing solution zone for adding a developing solution containing a specimen and a genetic recombinant TP antigen labeled with a radioisotope, a latex, metal colloid particles, fluorescent particles or colored particles, a detection zone in which a TP antigen is immobilized to a matrix which can transfer a solution by capillarity and a developing solution-absorbing zone are provided on the matrix; adding a specimen solution to the specimen dotting zone; supplying a developing solution to the developing solution zone; and detecting the labeled substance immobilized to the detection zone in an amount depending on the anti-TP antibody in the specimen solution.

DESCRIPTION OF THE PREFERRED EMBODIMENTS

Figure 1:
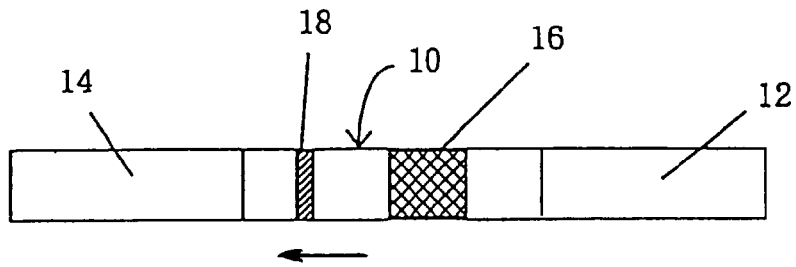
FIG. 1 is a view showing one example of an embodiment of the immunoassay device using a labeled substance pad of the present invention schematically.

In the following, the present invention is explained in detail. Incidentally, in the drawings, distances between portions or zones disposed on a membrane or a matrix are not the exact one. That is, the respective portion or zone shown in the respective drawing merely shows the relative relationship in the position thereof.

Figure 2:
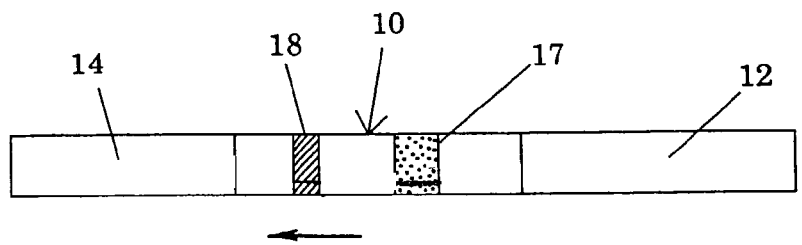
FIG. 2 is a view showing the immunoassay device in which a labeled substance is dotted to a membrane portion of the present invention schematically.
Figure 11:
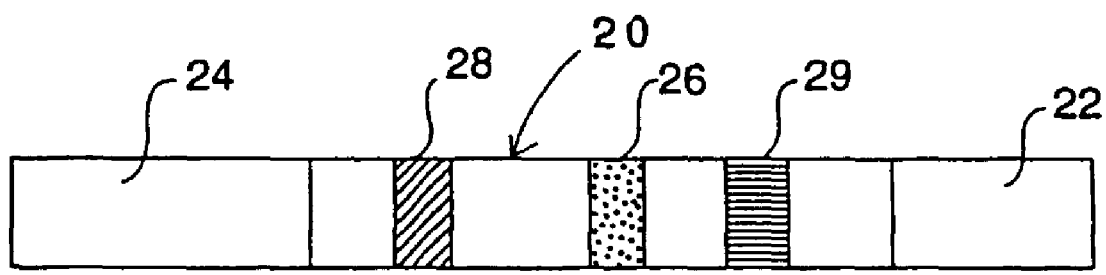
FIG. 11 is a view showing a conventional immunoassay device schematically.

A preferred first embodiment of the immunoassay device of the present invention is schematically shown in FIG. 1 and FIG. 2. A basic constitution thereof is the same as that of the above conventional assay device shown in FIG. 11. That is, the assay device of the present invention has a membrane portion 10. As in the prior art, the membrane portion 10 generally comprises a material such as a membrane formed from nitrocellulose, cellulose or glass fiber and generally has a rectangular shape. At both ends of the membrane portion 10, a developing solution-supplying portion 12 and a water absorption portion 14 are provided, respectively. As in the prior art, in these portions, a membrane can be elongated, or a water-absorbable material such as a sponge, a water-absorbable nonwoven fabric and a filter paper can be added. The developing solution-supplying portion 12 and the water absorption portion 14 are generally formed to be thicker than the membrane portion 10 so that they can be impregnated with a large amount of a liquid, which, however, is not indispensable. A detection portion 18 is provided between a labeled substance dotting portion 16 or 17 (described below) provided on the membrane portion 10 and the water absorption portion 14. As in the prior art, to the detection portion 18 is immobilized an antibody or antigen which reacts with an antigen or antibody to be detected. As in the prior art, the detection portion 18 is preferably formed to have a linear shape (line(s)), but the shape is not necessarily linear and may be other shape such as a round shape. When the detection portion 18 comprises a linear shape, in addition to the line which detects an analyte (antigen or antibody), a control line which is colored such as red, blue, etc., for confirming development of a developing solution reaching said portion may be also provided at the downstream side of the developing solution than the line for detection. Also, as in the prior art, the membrane portion 10 is blocked with BSA (bovine serum albumin) or the like in order to prevent nonspecific adsorption of protein.

In the assay device of the first embodiment shown in FIG. 2 of the present invention, the labeled substance dotting portion 17 is provided on the membrane portion 10. In the labeled substance dotting portion 17, a labeled substance in which an antibody or antigen which reacts with an antigen or antibody to be detected is labeled with an enzyme is contained in a dry state. In the assay device shown in FIG. 1 of the present invention, as the labeled substance dotting portion, a labeled substance pad 16 formed from a water-absorbable material, containing the labeled substance may be provided on the membrane portion 10. As in the prior art, as a labeling enzyme, there may be used alkaline phosphatase, peroxidase, β-galactosidase, β-glucosidase and the like which have been used frequently in immunoassay. Further, by binding the enzyme to the antigen or antibody by covalent bonding or non-covalent bonding, the labeled substance can be prepared.

The material of the labeled substance pad 16 is not particularly limited so long as it has water absorption property, and there may be mentioned a sponge, a water-absorbable nonwoven fabric and a filter paper. The size of the labeled substance pad 16 is not particularly limited, but it is generally a length and a width of about 3 to 10 mm and a thickness of about 0.5 mm to 4 mm. The amount of the labeled substance to be contained in the labeled substance pad 16 is not particularly limited so long as it is more than the amount in the case where the labeled substance is directly dotted to a conventional membrane and dried, and it is generally about 0.01 to 5 µg in terms of dry weight although it may vary depending on the respective tests.

When the device is used, a specimen solution is added to the labeled substance dotting portion 17 or the labeled substance pad 16, and a developing solution is added to the developing solution-supplying portion 12. The developing solution contains a substrate of the labeling enzyme of the labeled substance, which, for example, colors by an enzymatic reaction. The labeled substance contained in the labeled substance dotting portion 17 or the labeled substance pad 16 reacts with an antigen or antibody in the specimen solution, is flowed by the developing solution flowing from the developing solution pad 12 and reacts with the substrate in the developing solution to produce a pigment. When they are flowed by the developing solution and reach to the detection portion 18, the antigen or antibody in the specimen is trapped by an antibody or antigen immobilized to the detection portion 18 and held there. In this case, the antigen or antibody in the specimen is bound to the labeled substance so that the labeled substance is also held at the detection line(s) of the detection portion 18 and reacts with the substrate to effect pigmentation. Between the developing solution-supplying portion 12 and the detection portion 18, the substrate moves in the developing solution while it reacts with the labeled substance, and at the detection portion 18, a sufficient amount for carrying out immunoassay of the substrate is contained in the developing solution. Therefore, when the antigen or antibody to be detected is contained in the specimen solution, coloring is observed on the detection portion 18. The developing solution and the pigment and other components which are not trapped are absorbed into the absorption portion 14. On the other hand, when the antigen or antibody to be detected is not contained in the specimen solution, the labeled substance is not trapped at the detection portion 18 and therefore is absorbed as such into the absorption portion 14, whereby coloring is not observed on the detection portion 18. Thus, whether or not the antigen or antibody to be detected is contained in the specimen can be found by whether or not the detection portion 18 is colored.

As the substrate contained in the developing solution, there may be mentioned various coloring substrates corresponding to the above enzyme, for example, 3-indolyl derivatives such as 5-bromo-4-chloro-3-indolyl phosphate, 5-bromo-6-chloro-3-indolyl phosphate, 5-bromo-4-chloro-3-indolyl-β-D-galactopyranoside, 5-bromo-6-chloro-3-indolyl-β-D-galactopyranoside, 5-bromo-4-chloro-3-indolyl-β-D-glucopyranoside and 5-bromo-6-chloro-3-indolyl-β-D-galacto-pyranoside.

In the above explanation, as the substance to be labeled with the enzyme and the substance to be immobilized to the detection portion 18, an antibody or antigen is used. However, "an antibody or antigen" mentioned in the present specification includes an antibody fragment (e.g., a Fab fragment and a F(ab')$_2$ fragment), hapten and the like so long as they are substances by which an antigen-antibody reaction can be carried out.

In the assay device of the present invention, the specimen is sufficiently reacted with the labeled substance without dilution, and an immune complex of the labeled substance and the antigen or antibody in the specimen is formed. Further, in the assay device of the present invention, when the above labeled substance pad is used, the amount of the labeled substance to be contained can be made twice or more of a conventional amount, and as compared with the case where a labeled substance is directly dotted to a membrane and dried, the labeled substance is flowed more smoothly by the developing solution. Further, the amount of the specimen solution to be used can be increased to about five times of a conventional amount. That is, in an assay device using a labeled substance pad, even when a large amount of a specimen solution is added to a labeled substance dotting portion, a membrane cannot absorb a large amount of the specimen solution so that the specimen solution is protuberant on the membrane and flowed out to the outside of the device. The specimen solution cannot be utilized effectively, and it is meaningless to use a large amount of the specimen. Therefore, the amount of the specimen solution to be added is generally about 5 µl, and not a conventional dropping pipette, but a special dispenser is used. To the contrary, in the assay device using a labeled substance pad of the present invention, the specimen solution is added to the water-absorbable labeled substance pad so that as compared with a conventional case where a specimen solution is added to the specimen dotting portion 29 which is a membrane, a larger amount of the specimen solution can be absorbed. By the above facts, in the assay device of the present invention, detection sensitivity is high, and an accurate test can be carried out within a shorter period of time as compared with the conventional device. Further, about 25 µl of the specimen solution can be added so that a conventional dropping pipette can be used, which results in a simple and easy operation.

Figure 3:
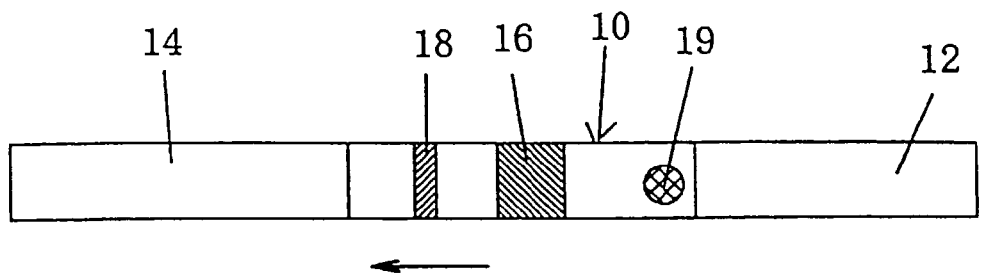
FIG. 3 is a view showing one example of a preferred embodiment of the immunoassay device of the present invention schematically.

A preferred second embodiment of the immunoassay device of the present invention is schematically shown in FIG. 3. A basic constitution thereof is also the same as that of the above assay device shown in FIG. 2.

In the labeled substance-containing portion 16, a labeled substance in which an antibody or antigen which reacts with an antigen or antibody to de detected is labeled with an enzyme is contained in a dry state. As in the prior art, as a labeling enzyme, there may be used alkaline phosphatase, peroxidase, β-galactosidase and the like which have been used frequently in immunoassay. The labeled substance may be directly dotted to the membrane, or a labeled substance pad 16 comprising a water-absorbable material such as a sponge, a water-absorbable nonwoven fabric and a filter paper may be provided on the membrane, and the labeled substance may be incorporated into the labeled substance pad. In this case, the labeled substance can be contained in a larger amount, the labeled substance is easily flowed by a developing solution, and a large amount of a specimen solution can be used, whereby detection sensitivity can be heightened.

In the immunoassay device of the present invention, a substrate-containing portion 19 containing a substrate of the labeling enzyme in a dry state is provided on the membrane portion 10, which is different from the conventional devices. The amount of the substrate to be contained in the substrate-containing portion 19 is not particularly limited, but it is generally about 20 to 200 µg although it may vary depending on the respective tests. As in the prior art, the substrate is a substrate of a labeling enzyme, which colors by an enzymatic reaction.

When the device is used, a specimen solution is added to the labeled substance-containing portion 16, and a developing solution is added to the developing solution-supplying portion 12. In the developing solution, the substrate of the labeling enzyme of the labeled substance is not contained, which is different from the prior art.

The developing solution added to the developing solution-supplying portion 12 is flowed while dissolving the substrate in the substrate-containing portion 19 and reaches to the labeled substance-containing portion 16. The subsequent procedure are the same as those shown in FIG. 1.

In the conventional devices, the substrate is contained in the developing solution, and a large amount of the developing solution is used so that a coloring reaction continues for an indefinite period of time. To the contrary, in the assay device of the present invention, after the whole amount of the substrate contained in the substrate-containing portion 19 is flowed away by the developing solution, the substrate does not exist so that a coloring reaction does not proceed any more. Therefore, a result which was judged as negative at the time of judgment is not changed to positive with a lapse of time. Further, in the assay device of the present invention, the substrate is maintained in a dry state so that storage stability is high as compared with the case where the substrate is maintained as a liquid in the state of being dissolved in the developing solution as in the prior art.

Next, as the third embodiment of the present invention, the immunoassay method of the present invention is described in detail by referring to an immunoassay device. In the immunoassay device, a matrix 1 comprises a water-absorbable material which can transfer a solution by capillarity. A preferred material includes, for example, a cellulose or a derivative thereof such as cellulose and nitrocellulose, a filter paper formed from a glass fiber or the like and a porous film. The size of the matrix is not limited, but, for example, a strip-shaped matrix having a width of about 3 mm to 10 mm and a length of about 30 mm to 100 mm is preferred since its handling is easy. The thickness of the matrix is preferably 100 μm to 1 mm. A part of the matrix may be blocked with bovine serum albumin (BSA), casein, sucrose or the like in order to prevent adsorption of protein by a nonspecific reaction.

(Labeling Reagent Zone)

The labeling reagent zone 4 is a zone containing a labeled genetic recombinant TP antigen provided on the matrix 1. This zone can be provided at an upstream side of a solution transferring direction of a developing solution from a developing solution zone 2 than a detection zone 5. This zone can be provided by a method of dotting a labeled genetic recombinant TP antigen to the matrix 1 or a method of providing a water-absorbable pad containing a labeled genetic recombinant TP antigen on the matrix 1.

In the TP antigen, surface antigens having various molecular weights exist on the cell surface of TP, and as a main example, there have been known antigens having molecular weights of 47 kDa (TP47), 42 kDa (TP42), 17 kDa (TP17) and 15 kDa (TP15). Genes coding these antigens have already been cloned, and the antigens have been produced by genetic engineering (see PCT Provisional Patent Publication No. 500403/1990, INFECTION AND IMMUNITY, Vol. 57, No. 17, pp. 3708 to 3714, 1989 and Molecular Microbiology, 4(8), pp. 1371 to 1379, 1990).

The genetic recombinant TP antigen of the present invention can be prepared by culturing *Escherichia coli* which has been transformed by integrating the above antigen having the respective molecular weight into a vector according to the method of Norgard et al. (INFECTION AND IMMUNITY, Vol. 61, pp. 1202 to 1210, 1993) and carrying out purification from a culture solution by combining known methods. In the genetic recombinant TP antigen of the present invention, a derivative of the above antigen protein having the respective molecular weight exists. For example, a TP antigen in which glutathione-S-transferase (GST) is fused to the N end of protein, produced by genetic engineering (Japanese Provisional Patent Publication No. 287017/1995) may be used.

The genetic recombinant TP antigen is bound to a labeled substance to prepare a reagent. As the labeled substance, there may be mentioned, for example, an enzyme, a radioisotope, a latex, metal colloid particles, fluorescent particles and colored particles. As the enzyme, there may be mentioned various kinds of enzymes used in enzyme immunoassay (EIA), for example, alkaline phosphatase, peroxidase and β-D-galactosidase. As the radioisotope, there may be mentioned, for example, an isotope such as iodine, tritium and carbon. As the latex, there may be mentioned, for example, particles of a high molecular weight compound such as a polystyrene latex. The metal colloid particles are, for example, particles comprising various kinds of metal colloids, and there may be mentioned colloid of a metal such as selenium, platinum and gold. The particle size is preferably a diameter of 10 nm to 1 μm.

As the fluorescent particles, there may be mentioned, for example, particles of polystyrene, a styrene-butadiene copolymer, a styrene-acrylic acid copolymer or glass containing a fluorescent substance such as fluorescein, rhodamine and platinum cyanide. The colored particles are particles comprising an organic high molecular weight compound or an inorganic compound colored with various kinds of dyes or pigments and are constituted by using, for example, a material comprising one or a mixture of polystyrene, polymethyl acrylate, polyacrylamide, polypropylene, polycarbonate, glass and the like. The particle sizes of the above fluorescent particles and colored particles are preferably 10 nm to 1 μm.

The labeled substance and the genetic recombinant TP antigen can be bound by using a known method of forming a covalent bond or a non-covalent bond. As a binding method, there may be mentioned, for example, the glutaraldehyde method, the periodic acid method, the maleimide method, the pyridyl•disulfide method and a method using various kinds of crosslinking agents (see, for example, "Protein, Nucleic acid and Enzyme", special edition, No. 31, pp. 37 to 45 (1985)). In the binding method using a crosslinking agent, for example, N-succinimidyl-4-maleimide butyric acid (GMBS), N-succinimidyl-6-maleimide hexanoic acid and N-succinimidyl-4-(N-maleimidomethyl)cyclohexane-1-carboxylic acid may be used as a crosslinking agent. In the method by covalent bonding, a functional group existing in the genetic recombinant TP antigen can be used, and after introducing a functional group such as a thiol group, an amino group, a carboxyl group and a hydroxy group into the genetic recombinant TP antigen, a labeled genetic recombinant TP antigen can be prepared by the above binding method. As the method by non-covalent bonding, there may be mentioned the physical adsorption method.

A method for labeling the genetic recombinant TP antigen by using a radioisotope can be carried out by, for example, using a Bolton Hunter reagent.

The amount of the labeled genetic recombinant TP antigen to be contained in the labeling reagent zone may be changed suitably depending on a method for dotting it to the matrix or incorporating it into a water-absorbable pad, an object to be tested and the amount of a specimen used for measurement, but it is generally about 0.01 μg to 5 μg in terms of dry weight. As the labeled genetic recombinant TP antigen, at least one antigen selected from genetic recombinant TP antigens such as TP47, TP42, TP17 and TP15, which are labeled, may be used by adding it to the labeling reagent zone.

Further, the recombinant TP antigen may be a fusion antigen of syphilis treponema produced by fusing two or more antigens selected from the above-mentioned respective antigens, and includes, for example, TP15-17 antigen, TP15-42 antigen, TP15-47 antigen, TP17-42 antigen, TP17-47 antigen, TP-42-47 antigen, TP15-17-42 antigen, TP15-42-47 antigen, TP-15-17-47 antigen, TP17-42-47 antigen and TP15-17-42-47 antigen, or may be a fusion azntigen of syphilis treponema in which the order of bonding these antigens is changed.

(Specimen Dotting Zone)

Figure 5:
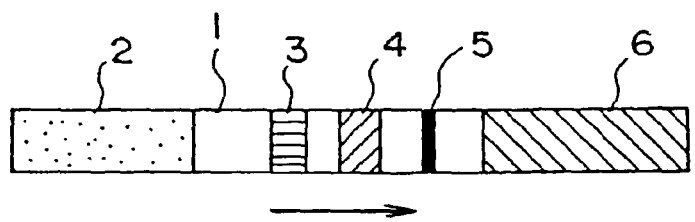
FIG. 5 is a plane view showing one example of an embodiment of the immunoassay device of the present invention.

A specimen dotting zone 3 can be provided without containing a reagent or the like, on the matrix 1 at a downstream side of the solution transferring direction of a developing solution from the developing solution zone 2 and yet an upstream side than the detection zone 5 (see FIG. 5). Further, the specimen dotting zone 3 can be provided at a downstream side of the solution transferring direction of a developing solution from the developing solution zone 2 and yet an upstream side than the labeling reagent zone 4, or at a downstream side than the labeling reagent zone 4 and yet an upstream side of the detection zone 5. In the above device in which a water-absorbable pad is provided on the labeling reagent zone 4, it is preferred to provide the specimen dotting zone 3 on said pad in order to carry out analysis with good efficiency (see FIG. 6). In the device to which the pad is added, a large amount of a specimen solution can be dotted so that a minute amount of a component in a specimen can be analyzed with high detection sensitivity. The water-absorbable pad may be constituted by using, for example, one or a combination of materials comprising porous synthetic or natural high molecular weight compounds such as polyvinyl alcohol (PVA), a nonwoven fabric and cellulose. The size and thickness of the pad is not limited, but it is generally preferred to use a pad having a length and a width of about 3 mm to 10 mm and a thickness of about 0.5 mm to 4 mm in order to carry out measurement with good efficiency.

Figure 10:
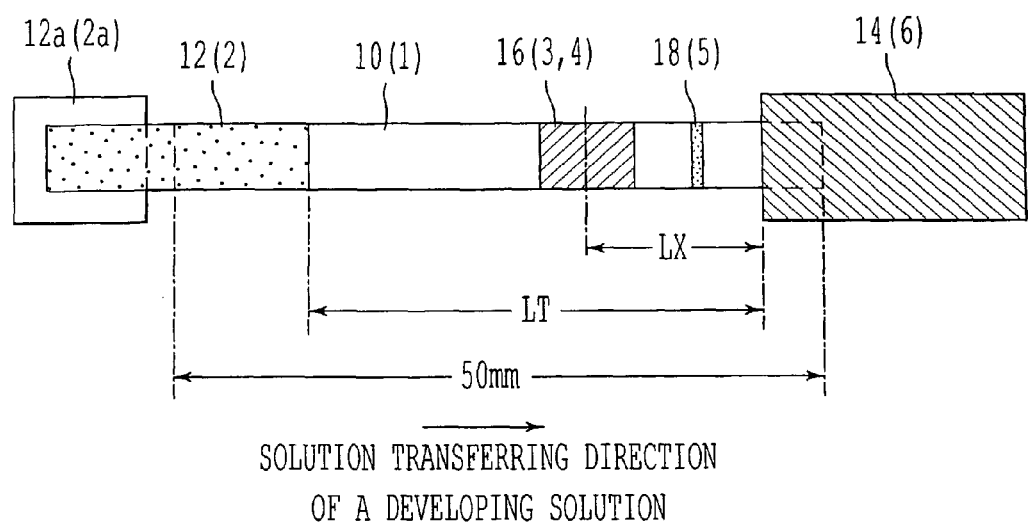
FIG. 10 is a plane view schematically showing an immunoassay device used for determination of a suitable position for a specimen dotting zone or portion.

Incidentally, as shown in FIG. 10, it is preferred to provide the specimen dotting zone 3 (or the labeled substance dotting portion 17 or the labeled substance pad 16 in the first and second embodiments) at a position where the ratio LX/LT is less than 0.5, wherein LX is the distance from the longitudinal center of the specimen dotting zone 3 (or the labeled substance dotting portion 16, 17 in the first and second embodiments) to an end of a developing solution-absorbing zone 6 (or the absorption portion 14 in the first and second embodiments), the end of which is present at an upstream side of the solution transferring direction of the developing solution, and LT is the distance from said end of said developing solution-absorbing zone (or said absorption portion) to an end of the developing solution zone 2 (or the developing solution-supplying portion 12 in the first and second embodiments), the end of which is present at a downstream side of the solution transferring direction of the developing solution. It is more preferable that the ratio LX/LT is present in the range of 0.34 to 0.46, most preferable 0.35 to 0.45.

(Detection Zone)

The detection zone 5 can be provided at an upstream side of the solution transferring direction of a developing solution from the developing zone 2 than the developing solution-absorbing zone 6 and yet a downstream side than the specimen dotting zone 3 by immobilizing the TP antigen. This zone can be provided by immobilizing the TP antigen to the matrix 1 by a method of chemical bonding such as covalent bonding or physical adsorption. Also, the TP antigen may be bound to an insoluble carrier and incorporated into the matrix 1. The insoluble carrier includes particles obtained by insolubilizing a mixture comprising gelatin, gum arabic and sodium hexamethaphosphate (Japanese Patent Publication No. 29223/1988), a polystyrene latex, red blood cells of various kinds of animals and a glass fiber. The insoluble carrier and the TP antigen can be bound by the above chemical bonding or physical adsorption. The detection zone 5 may have any shape, but in order to improve detection sensitivity, it is preferred that the detection zone 5 is formed in a linear shape so that it intersects the solution transferring direction of a developing solution perpendicularly, and the TP antigen is immobilized thereto.

The detection zone 5 can be formed by immobilizing the above genetic recombinant TP antigens such as TP47, TP42, TP17 and TP15 to the matrix 1, respectively. Two or more detection zones 5 can be provided by immobilizing the above antigens to different positions on the matrix 1, respectively. In the device in which two or more detection zones 5 are provided, antibodies to the respective antigens can be detected separately. Further, these two or more genetic recombinant TP antigens may be mixed to prepare one detection zone 5. Furthermore, in the detection zone 5, the so-called cultured TP antigen (see Japanese Provisional Patent Publication No. 71457/1983) obtained by decomposing cells of TP (Nicolle's strain) cultured in a living body such as a rabbit testicle according to a method known to a person skilled in the art and carrying out purification by using methods such as extraction and centrifugation in combination other than the genetic recombinant TP antigen may be used.

(Developing Solution Zone)

The developing solution zone 2 is a zone provided at one end of the matrix 1, to which a developing solution is supplied. Measurement can be started by dipping this zone in a container containing a developing solution at least in such an amount that the developing solution can reach to the developing solution-absorbing zone 6. Also, measurement can be also started by supplying a developing solution by adding a liquid reservoir 2a containing a developing solution to the developing solution zone 2 and breaking the liquid reservoir 2a to bring the developing solution into contact with the matrix. In the developing solution, a surfactant, a buffer and the like may be suitably contained. As a buffer solution containing a buffer, there may be mentioned, for example, an acetate buffer solution, a borate buffer solution, a Tris-HCl buffer solution and a diethanolamine buffer solution. A water-absorbable filter paper or the like may be further provided on the developing solution zone 2 depending on the supplying system of the developing solution.

(Developing Solution-absorbing Zone)

The developing solution-absorbing zone 6 is provided at one end opposite to the developing solution zone 2 provided at the other end of the matrix 1. This zone is provided for absorbing the developing solution supplied to the matrix 1 in order to carry out analysis smoothly. The developing solution-absorbing zone 6 can be also secured by forming a long matrix. Development can be accelerated by providing a water-absorbable material on the matrix 1. When the water-absorbable material is added, a filter paper, a sponge or the like having high water retention property comprising a natural high molecular weight compound, a synthetic high molecular weight compound or the like. By laminating the water-absorbable material on the matrix 1, an immunoassay device minimized in size can be prepared.

The device of the present invention can take various kinds of device forms depending on the kind of the labeled substance. However, when an enzyme is used as the labeled substance, the device is an immunoassay device for the anti-TP antibody, in which the developing solution zone 2 containing a substrate, the labeling reagent zone 4 comprising a genetic recombinant TP antigen labeled with an enzyme, the detection zone 5 in which a TP antigen is immobilized to the matrix 1 which can transfer a solution by capillarity, the specimen dotting zone 3 and the developing solution-absorbing zone 6 are provided on the matrix 1.

In the device using the above enzyme as the labeled substance, various kinds of substrates can be used for detection. The substrate is used generally by adding it to the developing solution. As the substrate, there may be used the following various kinds of coloring substrates, fluorescent substrates and light emission substrates depending on the enzyme.

(a) Coloring substrate for peroxidase: 2,2'-azino-bis(3-ethylbenzothiazolin-6-sulfonic acid) (ABTS), 3,3'-5,5'-tetramethylbenzidine (TMB) or diaminobenzidine (DAB) in combination with hydrogen peroxide;

for alkaline phosphatase: 5-bromo-4-chloro-3-indolyl-phosphoric acid (BCIP);

(b) Fluorescent substrate for alkaline phosphatase: 4-methylumbelliphenyl-phosphate (4MUP);

for β-D-galactosidase: 4-methylumbelliphenyl-β-D-galactoside (4MUG);

(c) Light emission substrate for alkaline phosphatase: disodium 3-(2'-spiro-adamantan)-4-methoxy-4-(3"-phosphoryloxy)phenyl-1,2-dioxetane (AMPPD);

for β-D-galactosidase: 3-(2'-spiroadamantan)-4-methoxy-4-(3"-D-galactopyranosyl)phenyl-1,2-dioxetane (AMGPD); and for peroxidase: luminol or isoluminol in combination of hydrogen peroxide.

The above substrate in the developing solution may be provided as a substrate zone 7 on the matrix 1. The substrate zone 7 provided on the matrix 1 can be formed generally by dissolving the substrate in a solution, adding the resulting solution to the matrix 1 and then drying the solution.

Further, as an embodiment of the device of the present invention, there may be mentioned an immunoassay device for the anti-TP antibody, in which a specimen developing solution zone for adding a developing solution containing a specimen and a genetic recombinant syphilis treponeme antigen labeled with a radioisotope, a latex, metal colloid particles, fluorescent particles or colored particles, a detection zone in which a TP antigen is immobilized to a matrix which can transfer a solution by capillarity and a developing solution-absorbing zone are provided on the matrix.

This assay device is different from the above device in that a specimen and a genetic recombinant TP antigen labeled with a radioisotope, a latex, metal colloid particles, fluorescent particles or colored particles are added to the specimen developing solution zone. The specimen developing solution zone can be formed by a method of adding a solution containing the above labeled genetic recombinant TP antigen and a solution containing a specimen, respectively, or a method of adding a mixed solution containing the labeled genetic recombinant TP antigen and a specimen. To the developing solution, a developing solution containing the above surfactant, buffer or the like may be added, if desired. The labeled genetic recombinant TP antigen to be added to the specimen developing solution zone is a genetic recombinant TP antigen labeled with a radioisotope, a latex, colloid particles or colored particles and may be selected from the labeled genetic recombinant TP antigens used in the above assay device. Further, the detection zone and the developing solution-absorbing zone of the assay device may be the same as those of the above assay device.

(Method of Use)

By using the assay device of the present invention, the anti-TP antibody in various kinds of specimens can be analyzed. When analysis is carried out by using the device, in the first place, a specimen is supplied to the matrix 1 of the device and developed with a developing solution. The developing solution reaches to the developing solution-absorbing zone 6 by capillarity, and components in the specimen and the labeled genetic recombinant TP antigen which are not bound to the detection zone 5 are absorbed to complete development. After development is finished, the labeled substance immobilized to the detection zone 5 in an amount depending on the anti-TP antibody in the specimen solution is directly or indirectly detected to analyze the anti-TP antibody. The detection can be carried out by visual observation with eyes or by using a measurement device such as a scintillation counter, a calorimeter, a fluorophotometer, a photocounter and a light-sensitive film depending on the labeled substance. In the analysis, a method of using, for example, an enzyme as the labeled substance and measuring presence or absence of a dye formed by a color emission substrate qualitatively visually with eyes is simple and easy. By this method, semi-quantitative analysis can be carried out by using a color chart corresponding to the concentration of the anti-TP antibody.

The matrix may be laminated on and fixed to a support member such as a plastic, a metal and a paper depending on the kind of the labeled substance. Further, by fixing the matrix 1 to a case made of a plastic or the like, providing a solution reservoir containing the developing solution on the developing solution zone 2 and laying covers each having a hole on the above respective zone portions, a device which can be handled easily can be constituted. In the immunoassay device of the present invention, the specimen is not particularly limited, and the device can be suitably used for detecting the anti-TP antibody in various kinds of body fluids such as serum, plasma, whole blood and urine.

EXAMPLES

The present invention is described in detail by referring to Examples. As a matter of course, the present invention is not limited by Examples described below.

Example 1

At both ends of a membrane portion 10 comprising a nitrocellulose membrane having a size of 5 mm×50 mm, a developing solution-supplying portion 12 and a water absorption portion 14 each comprising a water-absorbable nonwoven fabric were provided, respectively. An anti-HBs polyclonal antibody was dotted to a part of the membrane portion 1, which was near the water absorption portion 14, and dried to give a detection line 18. Then, after the membrane 10 was blocked, in the device A, a labeled substance pad 16 comprising a water-absorbable nonwoven fabric which was a square having a side length of 5 mm and a thickness of 1 mm was provided on the membrane. 10 μl of a solution containing an alkaline phosphatase-labeled anti-HBs monoclonal antibody at a concentration of 12.5 μg/ml was dotted to the labeled substance pad 16 and dried to prepare an assay device. On the other hand, in the device B, without providing a labeled substance pad 16, 5 μl of a solution containing an alkaline phosphatase-labeled anti-HBs monoclonal antibody at a concentration of 25 μg/ml was directly dotted to the membrane 10 and dried to prepare an assay device.

As specimen solutions, standard solutions containing a HBs antigen at a concentration of 0 to 90 ng/ml and a HBs-negative serum or HBs-positive sera diluted to 32 to 256 times were used. In the device A, 25 µl of these specimen solutions were added to the labeled substance pad 16, respectively, and in the device B, 5 µl of the specimen solutions were added to the labeled substance dotting portion 17, respectively. On the other hand, 200 µl of a developing solution was added to each developing solution-supplying portion 12. The developing solution contained toluidine 5-bromo-4-chloro-3-indolylphosphate which was a substrate, at a concentration of 1.5 mg/ml. Coloring at the detection line 18 at the time of 15 minutes, 30 minutes and 60 minutes after addition of the developing solution was observed. The results are shown in the following Table 1.

TABLE 1

| Assay device | | Judgment time | | | | | |
|---|---|---|---|---|---|---|---|
| | | 15 minutes | | 30 minutes | | 60 minutes | |
| | | A | B | A | B | A | B |
| Concentration of antigen in Standard solution (ng/ml) | 0 | – | – | – | – | – | – |
| | 5 | – | – | – | – | + | – |
| | 10 | – | – | + | – | + | – |
| | 30 | + | – | + | – | + | + |
| | 90 | + | ± | + | + | + | + |
| Negative serum | | – | – | – | – | – | – |
| Positive serum diluted to 256 times | | – | – | ± | – | + | ± |
| Positive serum diluted to 128 times | | ± | – | + | – | + | + |
| Positive serum diluted to 64 times | | + | – | + | ± | + | + |
| Positive serum diluted to 32 times | | + | + | + | + | + | + |

In Table 1, "–" means that coloring was not observed on the detection line 18, "+" means that coloring was clearly observed on the detection line 18; and "±" means that coloring was not clearly oberved, but was barely observed.

Example 2

To a membrane 10 comprising a nitrocellulose membrane, a developing solution pad 12 and a water-absorption pad 14 were provided, respectively, in the same manner as in Example 1. A HBs antigen (0.75 µg) was dotted to a part of the membrane portion 10, which was the same dotting portion as the anti-HBs polyclonal antibody, and dried to give a detection line 18. Then, after the membrane 10 was blocked, in the device C, a labeled substance pad 16 comprising a water-absorbable nonwoven fabric which was a square having a size of 6 mm×10 mm and a thickness of 0.5 mm was provided on the membrane. 5 µl (200 ng) of an alkaline phosphatase-labeled anti-HBs antigen was dotted to the labeled substance pad 16 and dried to prepare an assay device.

Also, in the device D, without providing a labeled substance pad 16, the above-mentioned labeled HBs antigen was dotted to the membrane 10 and dried to prepare an assay device.

As specimen solutions, standard solutions containing an anti-HBs antibody at a concentration of 0 to 64.5 mIU/ml were used. In the above-mentioned assay devices C and D, developments were carried out. Coloring at the detection line 18 at the time of 11 minutes, 15 minutes and 20 minutes after addition of the developing solution was observed. The results are shown in the following Table 2.

TABLE 2

| Assay device | | Judgment time | | | | | |
|---|---|---|---|---|---|---|---|
| | | 11 minutes | | 15 minutes | | 20 minutes | |
| | | C | D | C | D | C | D |
| Concentration of antibody in standard solution (mIU/ml) | 0 | – | – | – | – | – | – |
| | 15.6 | – | – | + | – | + | + |
| | 26.6 | – | – | + | – | + | + |
| | 64.5 | + | – | + | + | + | + |

"–" and "+" mean the same judgment standard as in Table 1.

Example 3

At both ends of a membrane portion 10 comprising a nitrocellulose membrane having a size of 5 mm×50 mm, a developing solution pad 12 and a water-absorption pad 14 each comprising a water-absorbable nonwoven fabric were provided, respectively. An anti-hemoglobin polyclonal antibody was dotted to a part of the membrane portion 10, which was near the water-absorption pad 14, and dried to give a detection line 18. Then, after the membrane 10 was blocked, a labeled substance pad 16 comprising a water-absorbable nonwoven fabric which was a square having a side length of 5 mm and a thickness of 1 mm was provided on the membrane. 10 µl of a solution containing an alkaline phosphatase-labeled anti-hemoglobin polyclonal antibody at a concentration of 15 µg/ml was dotted to the labeled substance pad 16 and dried. Further, in the device of Example 1, a substrate-containing portion 19 was provided on the membrane portion 10 between the labeled substance pad 16 and the developing solution pad 12 to prepare an assay device. The substrate-containing portion 19 was formed by repeating an operation of dotting 5 µl of a solution containing 20 mg/ml of sodium 5-bromo-4-chloro-3-indolyl-phosphate (BCIP, Na) and drying the solution three times.

Example 4

On the other hand, in the device of Example 4, a substrate-containing portion 19 was not provided.

After 25 µl of a sample containing 5, 10 or 20 ng/ml of hemoglobin was dotted to the labeled substance pad 16, 200 µl of a developing solution was added to the developing solution pad 12 to start measurement. As the developing solution, a solution comprising a 0.1 M 2,2'-iminodiethanol-phosphate buffer solution (pH 10), 1 mM $MgCl_2$ and 0.05% Tween 20 (trade name, produced by Atlas Powder Co.) was used. In Example 4, a solution obtained by adding BCIP, Na to the developing solution used in Example 3 at a concentration of 0.3 mg/ml was used as the developing solution. A judgment time was 8 minutes after the developing solution were added, and judgment was further carried out 10 minutes and 30 minutes after the starting point. The respective tests were carried out twice, respectively. The results are shown in Table 3 and Table 4.

TABLE 3

Results of Example 3

| Judgment time (min) | Hemoglobin concentration | | |
|---|---|---|---|
| | 20 ng/ml | 10 ng/ml | 5 ng/ml |
| 8 | ++ | -- | -- |
| 10 | ++ | ±- | -- |
| 30 | ++ | ±- | -- |

TABLE 4

Results of Example 4

| Judgment time (min) | Hemoglobin concentration | | |
|---|---|---|---|
| | 20 ng/ml | 10 ng/ml | 5 ng/ml |
| 8 | -- | -- | -- |
| 10 | ±± | -- | -- |
| 30 | ++ | ++ | ++ |

It can be seen that when the device of Example 4 was used, the judgment results were changed from negative to positive with a lapse of time, and when the device of Example 3 was used, there was almost no change in judgment from negative to positive. Thus, when a reaction is terminated after a certain reaction time and measurement is not carried out with a lapse of time, it is preferred to use the device of Example 3.

Comparative Example 1

Figure 4:
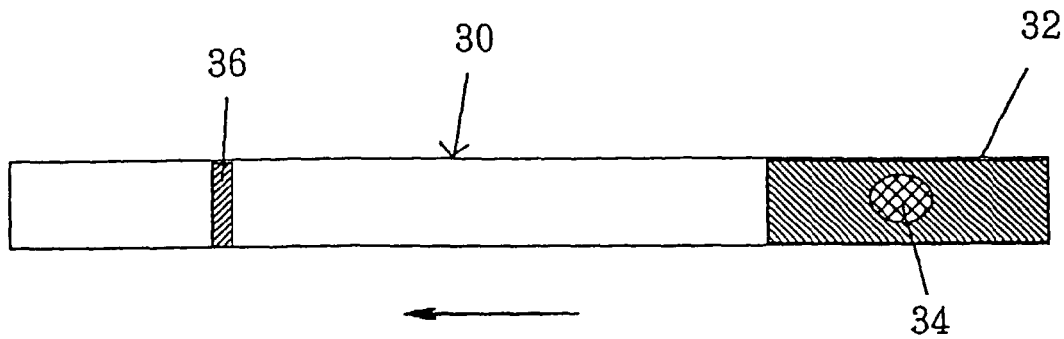
FIG. 4 is a view showing an immunoassay device using a color latex schematically.

A conventional assay device using a color latex as shown in FIG. 4 was prepared. A detection line 18 was prepared in the same manner as in Example 3. 100 μl of the same specimen solution as in Example 3 was added to a sample dotting position to start measurement. A judgment time was 8 minutes after the sample was added, and judgment was further carried out 10 minutes and 30 minutes after the starting point. The results are shown in Table 5.

TABLE 5

Results of Comparative example 1

| Judgment time (min) | Hemoglobin concentration | | |
|---|---|---|---|
| | 20 ng/ml | 10 ng/ml | 5 ng/ml |
| 8 | ±± | -- | -- |
| 10 | ±± | -- | -- |
| 30 | ++ | ++ | ±± |

From Table 5, it can be seen that even in the conventional method using a color latex, the judgment results were changed from negative to positive.

Example 5

Preparation of a Genetic Recombinant TP17 Antigen Labeled with Alkaline Phosphatase 200 nmol of 2-iminothiolan was added to 0.12 mg of a genetic recombinant TP17 antigen to which GST was bound, prepared according to the method described in Japanese Provisional Patent Publication No. 287017/1995, and the mixture was left to stand at 30° C. for 60 minutes to obtain a TP antigen into which thiol was introduced. Next, 300 nmol of N-succinimidyl-4-maleimide butyric acid (GMBS) was added to 3 mg of alkaline phosphatase, and the mixture was left to stand at 30° C. for 60 minutes to obtain alkaline phosphatase into which maleimide was introduced. Thereafter, 100 μg of the TP antigen into which thiol was introduced and 2.5 mg of alkaline phosphatase into which maleimide was introduced were mixed, and the mixture was reacted at 4° C. overnight. By using a gel filtration column, unreacted antigen and enzyme were removed to obtain an alkaline phosphatase-labeled genetic recombinant TP17 antigen.

Example 6

Device for Analyzing an Anti-TP17 Antibody

Figure 6:
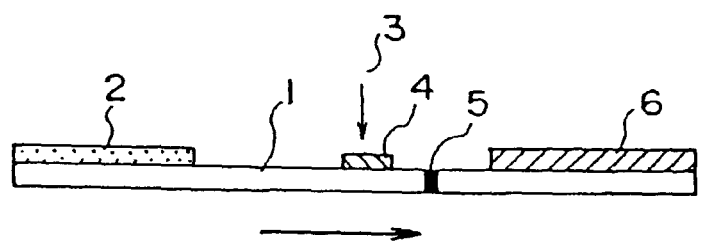
FIG. 6 is a sectional view of the immunoassay device of the present invention when a labeling reagent zone comprising a pad containing a labeled genetic recombinant TP antigen is added.
Figure 7:
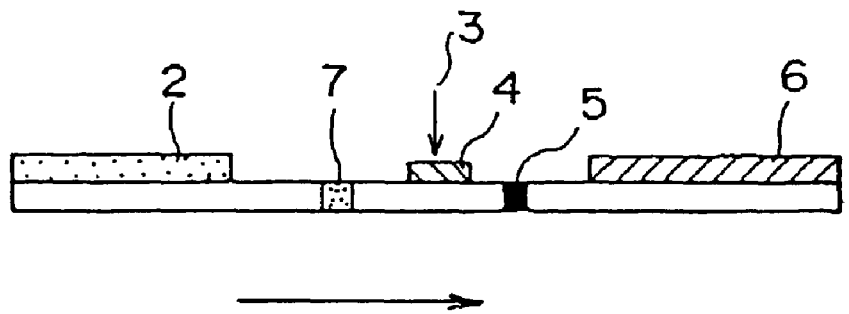
FIG. 7 is a sectional view of the immunoassay device of the present invention when a substrate zone 7 is provided on a matrix 1.

As shown in FIG. 6, at a position of 15 mm from the top end of a matrix 1 which was a cellulose film (produced by Millipore Co.) having a width of 5 mm and a length of 50 mm, the top end of which is present at a downstream side of the solution transferring direction of the developing solution, the same genetic recombinant TP17 antigen used in Example 5 was dotted in a line state by a coating device and then dried to prepare a detection zone 5. 20 μl of a solution containing the alkaline phosphatase-labeled genetic recombinant TP17 antigen prepared in Example 5 was dotted to a polyvinyl alcohol (PVA) sheet cut so as to have a width of 5 mm and a length of 5 mm and then dried to prepare a pad. The pad was placed at a position of 25 mm from the top end of the matrix 1 to prepare a labeling reagent zone 4 and a specimen dotting zone 3. At a position of 10 mm from the bottom end of the matrix 1, the bottom end of which is present at an upstream side of the solution transferring direction of the developing solution, a filter paper (produced by Millipore Co.) having a width of 5 mm and a length of 20 mm was provided to prepare a developing solution zone 2. Further, as a developing solution-absorbing zone 6, a filter paper having a width of 10 mm, a length of 20 mm and a thickness of about 1 mm was provided at a position of 10 mm from the top end of the matrix 1 to obtain a device for analyzing an anti-TP17 antibody.

Example 7

Measurement of an Anti-TP17 Antibody

An anti-TP antibody was analyzed by using the assay device prepared in Example 6. In the first place, 15 μl of a specimen was dotted to the specimen dotting zone 3, 200 μl of a solution containing 0.3% 5-bromo-4-chloro-3-indolyl-phosphoric acid (BCIP) was added dropwise to the developing solution zone 2 to effect absorption and development. After 15 minutes, the coloring degree of the detection zone 5 was judged visually with eyes. 89 human serum specimens were measured, and the results are shown in Table 6. A case where coloring was observed was judged as positive, and a case where coloring was not observed was judged as negative.

Also, with respect to the same specimen, a diluted series was prepared and measured by using a conventional indirect agglutination immunoassay reagent Serodia-TP•PA (registered trade name, produced by Fujirebio Inc.) for the anti-TP antibody. The results are shown in Table 6.

Example 8

Measurement of an Anti-TP47 Antibody

By using a recombinant TP47 antigen prepared according to the method of Norgard et al. (INFECTION AND IMMU- NITY, Vol. 61, pp. 1202 to 1210, 1993) and then purified, an alkaline phosphatase-labeled recombinant TP47 antigen was prepared and further a device for analyzing an anti-TP47 antibody was obtained according to the methods of Examples 5 and 6. By using the device, specimens shown in Table 6 were measured. The results of Examples 7 and 7 are shown in Table 6. When the specimens of Examples 7 and 8 giving a positive result in at least one of the devices were judged as positive, the same results as those obtained by the indirect agglutination method were obtained in all of the specimens.

TABLE 6

| Indirect agglutination Method (dilution ratio) | Assay device for TP17 antibody Positive specimen/ tested specimen (positive rate; %) | Assay device for TP17 and TP47 antibodies (positive rate; %) |
|---|---|---|
| Negative specimen (>1:80) | 0/28 (0) | (0) |
| Positive specimen (1:80) | 2/2 (100) | (100) |
| Positive specimen (1:160) | 3/3 (100) | (100) |
| Positive specimen (1:320) | 15/15 (100) | (100) |
| Positive specimen (1:640) | 5/6 (83.3) | (100) |
| Positive specimen (1:1280) | 9/9 (100) | (100) |
| Positive specimen (1:2560) | 8/8 (100) | (100) |
| Positive specimen (1:2560<) | 18/18 (100) | (100) |

Example 9

Device for Analyzing an Anti-TP17 Antibody and an Anti-TP47 Antibody

Figure 8:
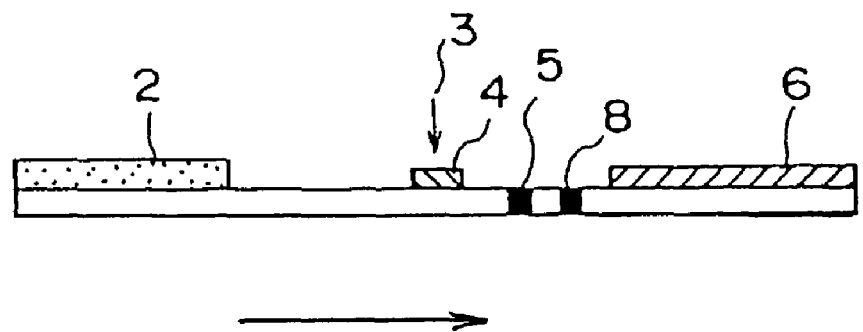
FIG. 8 is a sectional view of the immunoassay device of the present invention when two detection zones 5 and 8 are provided on a matrix.
Figure 9:
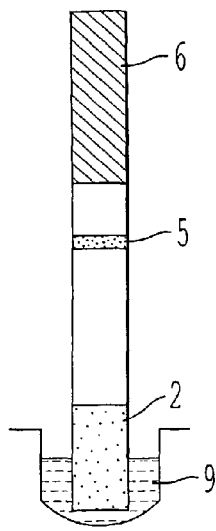
FIG. 9 is a plane view of the immunoassay device of the present invention when measurement is carried out by supplying a mixed solution 9 of a specimen and a genetic recombinant TP antigen labeled with a radioisotope, a latex, metal colloid particles, fluorescent particles or colored particles to a developing solution zone 2.

As shown in FIG. 8, at a position of 12 mm from the top end of a matrix 1 which was a cellulose film (produced by Millipore Co.) having a width of 5 mm and a length of 50 mm, a recombinant TP17 antigen was dotted in a line state by a coating device, and at a position of 17 mm from the top end of the matrix 1, the top end of which is present at a downstream side of the solution transferring direction of the developing solution, a genetic recombinant TP47 antigen was dotted in a line state by a coating device. The antigens coated were dried to prepare detection zones 5 and 8. 20 μl of a mixed solution containing the alkaline phosphatase-labeled recombinant TP17 antigen prepared in Example 5 and the alkaline phosphatase-labeled recombinant TP47 antigen prepared in Example 7 was dotted to a PVA sheet cut so as to have a width of 5 mm and a length of 5 mm and then dried to prepare a conjugate pad. The conjugate pad was placed at a position of 25 mm from the top end of the matrix 1 to prepare a labeling reagent zone 4. Paper filters of a developing solution zone 2 and a developing solution-absorbing zone 6 were provided in the same manner as in Example 6 to prepare a device for analyzing an anti-TP17 antibody and an anti-TP47 antibody.

Example 10

Measurement of an Anti-TP17 Antibody and an Anti-TP47 Antibody

With respect to the specimens giving a positive result by the indirect agglutination immunoassay method, anti-TP antibodies were measured by using the device prepared in Example 9. In the first place, 15 μl of a specimen was added to the specimen dotting zone 3 provided on the labeling reagent zone 4, and 200 μl of a solution containing 0.3% BCIP was added dropwise to the developing solution zone 2 to effect absorption and development. After 15 minutes, the coloring degrees of the detection zones 5 and 8 were judged visually with eyes. A case where coloring was observed was judged as positive, and a case where coloring was not observed was judged as negative.

The specimens judged as positive or negative by the above indirect agglutination immunoassay reagent were measured by the assay device of Example 9. The results are shown in Table 7. Further, a primary stage syphilis-infected specimen, a secondary stage infected specimen and a tardive stage infected specimen which were known were measured by using the indirect agglutination immunoassay and the assay device of Example 8, respectively. The results are shown in Table 8.

TABLE 7

| Specimen | Indirect agglutination method | Assay device for analyzing TP17 and TP47 antibodies | |
|---|---|---|---|
| | | TP17 | TP47 |
| 1 | + | + | + |
| 2 | + | + | − |
| 3 | + | − | + |
| 4 | − | − | − |

+: positive judgment,
−: negative judgment

TABLE 8

| Specimen | Indirect agglutination method | Assay device for analyzing TP17 and TP47 antibodies | |
|---|---|---|---|
| | | TP17 | TP47 |
| Primary stage syphilis-infected specimen | + | ± | + |
| Secondary stage syphilis-infected specimen | + | + | ± |
| Tardive stage syphilis-infected specimen | + | + | ± |

+: positive judgment,
±: weak positive judgment

Example 11

Preparation of Alkaline Phosphatase-labeled TP15-17 Antigen

A genetic recombinant TP15-17 antigen in which a TP15 antigen and a TP17 antigen were fused was prepared, and according to the same manner as in Example 5, an alkaline phosphatase-labeled TP15-17 antigen was obtained.

Example 12

Device for Analyzing an Anti-TP15-17 Antibody

According to the same manner as in Example 6, the alkaline phosphatase-labeled TP15-17 antigen prepared in Example 11 and the genetic recombinant TP15-17 antigen were dotted onto a matrix 1 to prepare a device for analyzing an anti-TP15-17 antibody.

Example 13

Device for Analyzing an Anti-TP15-17 Antibody

By using the analyzing device prepared in Example 12, analysis of an anti-TP antibody was carried out about 5 specimens of human sera according to the method of Example 7. The results are shown in Table 9.

Further, with regard to the same specimens, the results according to the above-mentioned indirect agglutination immunoassay reagent and anti-TP 47 antibody analyses are also shown in Table 9.

TABLE 9

| Specimen | Indirect agglutination immunoassay reagent | TP15–17 Antibody assay device | TP47 antibody assay device |
|---|---|---|---|
| 1 | + | + | + |
| 2 | + | + | + |
| 3 | +/− | + | − |
| 4 | +/− | + | − |
| 5 | − | − | − |

+: positive judgment,
+/−: judgment reserved,
−: negative judgment

Example 14

Determination of a Suitable Position for a Specimen Dotting Portion or Zone

As shown in FIG. 10, at a position of 5 mm from an end of a water absorption portion 14 (or a developing solution absorbing zone 6) which was a filter paper (produced by Whatman) having a width of 10 mm, a length of 20 mm and a thickness of 1 mm, the end of which was present at a downstream side of the solution transferring direction of a developing solution, wherein the water absorption portion 14 (or the developing solution absorbing zone 6) was provided at the right side region on a membrane 10 (or a matrix 1) which was a nitrocellulose film (produced by Millipore) having a width of 5 mm and a length of 50 mm, an anti-HBs rabbit polyclonal antibody was dotted in a line state by a coating device and then dried to prepare a detection portion 18 (a detection zone 5). On the other hand, at a position of 35 mm (hereinafter referred to as LT) from said end of said water absorption portion, an end of a developing solution-supplying portion 12 (or a developing solution zone 2) which was a glass fiber sheet AP-25 (produced by Millipore) having a width of 5 mm and a length of 20 mm and containing 100 μg of 5-bromo-4-chloro-3-indolylphosphate as a substrate in a dry state was contained, the end of which is present at a downstream side of the solution transferring direction of the developing solution, was provided at the left side region on the membrane 10 (or the matrix 1). Onto the developing solution-supplying portion 12 (or the developing solution zone 2), a reservoir 12a (2a) containing a developing solution therein was also attached. Further, a labeled substance pad 16 to which 5 μl of a solution containing 0.16 μg of an alkaline phosphatase-labeled anti-HBs mouse monoclonal antibody was dotted and then dried, was provided between the detection portion 18 (the detection zone 5) and the developing solution-supplying portion 12 (or the developing solution zone 2) on the membrane 10.

As a specimen solution, a HBs-positive serum (16.4 IU/ml) was used. In this device, each 25 μl of the specimen solution was added to a labeled substance pads 16 (or a labeling reagent zone 4) which were prepared so that the centers of said labeled substance pads (or said labeling reagent zone) are present at positions of 11, 12, 13, 14, 15, 16, 17, 18 and 19 mm (hereinafter referred to as LX) from the end of said water absorption portion (or said developing solution absorbing zone), respectively. After addition of the specimen solution, it was left for 15 seconds and then the developing solution was supplied to the membrane 10. Detection times were measured and coloring conditions at the detection portion 18 (or the detection zone) and the background thereof at the time of 15 minutes after supplying the developing solution were observed, respectively. The results are shown in the following Table 10.

TABLE 10

| Run | Position of pad 16 (LX:mm) | Detection Time | Coloring at the line 18 | Coloring at the background |
|---|---|---|---|---|
| 1 | 11 | 0 | 1 | 2 |
| 2 | 12 | 4 | 1 | 2 |
| 3 | 13 | 5 | 3 | 3 |
| 4 | 14 | 3 | 3 | 3 |
| 5 | 15 | 4 | 3 | 3 |
| 6 | 16 | 2 | 2 | 1 |
| 7 | 17 | 2 | 2 | 1 |
| 8 | 18 | 0 | 2 | 1 |
| 9 | 19 | 1 | 2 | 1 |

In Table 10, numerals in respective column show the following meaning.

1. Detection time
"0": impermissible (more than 12 minutes);
"1": more than 11.5 minutes and less than or equal to 12 minutes;
"2": more than 11 minutes and less than or equal to 11.5 minutes
"3": more than 10.5 minutes and less than or equal to 11 minutes;
"4": more than 10 minutes and less than or equal to 10.5 minutes; and
"5": less than 10.5 minutes.
2. Coloring at the line 18
"1": weak coloring but visible;
"2": visible; and
"3": clearly visible.
3. Coloring of background
"1": strong and thereby colored line is indistinguishable;
"2": present but colored line is distinguishable; and
"3": colored line is clearly distinguishable.

The present invention can provide an immunoassay device in which detection sensitivity is more excellent than that of a conventional immunoassay device.

The present invention can also provide an immunoassay device in which a judgment result at the time of judgment is not changed from negative to positive with a lapse of time, and an immunoassay method using the same.

The present invention further provides a method for analyzing the anti-TP antibody in a specimen simply and easily with high sensitivity. In this method, for example, the anti-TP antibody in serum can be analyzed within about 15 minutes to obtain a result. Prozone phenomenon observed at the time of measuring a specimen having a high antibody value of the anti-TP antibody was not observed in the assay method of the present invention. Further, when the method of the present invention is used, a plurality of the anti-TP antibodies in a specimen can be analyzed separately so that a stage of infection can be estimated, and the method is also useful for treating syphilis.

The invention claimed is:

1. An immunoassay device for detecting an anti-syphilis treponeme antibody in a specimen which comprises a matrix which can transfer a solution by capillarity, wherein the following are disposed on the matrix:
   (1) a specimen dotting zone,
   (2) a labeling reagent zone comprising a labeled genetic recombinant syphilis treponeme antigen, wherein the labeling reagent zone is downstream of the specimen dotting zone or the specimen dotting zone is provided on the labeling reagent zone, and the genetic recombinant syphilis treponeme antigen is at least one selected from the group consisting of a TP 15 antigen having a molecular weight of 15 kpa, a TP17 antigen having a molecular weight of 17 kDa, a TP42 antigen having a molecular weight of 42 kDa and a TP47 antigen having a molecular weight of 47 kDa and a fusion antigen of syphilis treponema in which two or more above syphilis treponeme antigens are fused,
   (3) at least two detection zones each comprising an immobilized genetic recombinant syphilis treponeme antigen which binds a complex formed between the anti-syphilis treponeme antibody and the labeled genetic recombinant syphilis treponeme antigen, wherein
   the detection zones are downstream of the labeling reagent zone and
   in one of the at least two detection zones, the genetic recombinant syphilis treponeme antigen is a TP47 antigen having a molecular weight of 47 kDa, and
   in the other of the at least two detection zones, the genetic recombinant syphilis treponeme antigen is at least one selected from the group consisting of a TP 15 antigen having a molecular weight of 15 kDa, a TP17 antigen having a molecular weight of 17 kDa, a TP42 antigen having a molecular weight of 42 kDa and a fusion antigen of syphilis treponema in which two or more above syphilis treponeme antigens are fused.

2. The device according to claim 1, wherein the specimen dotting zone is provided on the labeling reagent zone.

3. The device according to claim 1, wherein the labeling reagent zone is a water-absorbable pad containing the labeled genetic recombinant syphilis treponeme antigen on the matrix, and the specimen dotting zone is disposed on the labeling reagent zone, and said label is an enzyme.

4. The device according to claim 1, wherein the labeled genetic recombinant syphilis treponeme antigen is labeled with a label selected from the group comprising, a radioisotope, a latex, metal colloid particles, fluorescent particles or colored particles.

5. The device according to claim 1, wherein the labeling reagent zone is a water-absorbable pad containing the labeled genetic recombinant syphilis treponeme antigen to which a specimen is added, on the matrix, and the specimen dotting zone is disposed on the labeling reagent zone, and said label is selected from the group comprising a radioisotope, a latex, metal colloid particles, fluorescent particles or colored particles.

6. The device according to claim 1, wherein the device has a specimen developing solution zone for adding a developing solution containing a specimen and a genetic recombinant syphilis treponeme antigen labeled with a label selected from the group comprising a radioisotope, a latex, metal colloid particles, fluorescent particles or colored particles, and a developing solution-absorbing zone, all of which are disposed on the matrix.

7. The device according to claim 1, wherein the device has a developing solution zone upstream of the labeling reagent zone and a developing solution absorbing zone downstream of the detection zones.

8. The device according to claim 7, wherein the developing solution zone contains a substrate, and the labeled genetic recombinant syphilis treponeme antigen is labeled with an enzyme.

9. The device according to claim 7, wherein the device has a substrate zone on the matrix, and the labeled genetic recombinant syphilis treponeme antigen is labeled with an enzyme.

10. The device according to claim 7, wherein the specimen dotting zone is disposed on the labeling reagent zone.

11. The device according to claim 8, wherein the specimen dotting zone is disposed on the labeling reagent zone.

12. The device according to claim 9, wherein the specimen dotting zone is disposed on the labeling reagent zone.

13. The device according to claim 7, wherein the labeling reagent zone is a water-absorbable pad containing the labeled genetic recombinant syphilis treponeme antigen labeled on the matrix, and the specimen dotting zone is disposed on the labeling reagent zone, and said label is an enzyme.

14. The device according to claim 8, wherein the labeling reagent zone is a water-absorbable pad containing the labeled genetic recombinant syphilis treponeme antigen on the matrix, and the specimen dotting zone is disposed on the labeling reagent zone, and said label is an enzyme.

15. The device according to claim 9, wherein the labeling reagent zone is a water-absorbable pad containing the labeled genetic recombinant syphilis treponeme antigen on the matrix, and the specimen dotting zone is disposed on the labeling reagent zone, and said label is an enzyme.

16. The device according to claim 7, wherein the labeled genetic recombinant syphilis treponeme antigen is labeled with a label selected from the group comprising a radioisotope, a latex, metal colloid particles, fluorescent particles or colored particles.

17. The device according to claim 16, wherein the labeling reagent zone is a water-absorbable pad containing the labeled genetic recombinant syphilis treponeme antigen, to which a specimen is added, on the matrix, and the specimen dotting zone is disposed on the labeling reagent zone, and said label is selected from the group comprising a radioisotope, a latex, metal colloid particles, fluorescent particles or colored particles.

* * * * *

UNITED STATES PATENT AND TRADEMARK OFFICE
CERTIFICATE OF CORRECTION

| | | |
|---|---|---|
| PATENT NO. | : 7,771,928 B2 | Page 1 of 1 |
| APPLICATION NO. | : 10/229020 | |
| DATED | : August 10, 2010 | |
| INVENTOR(S) | : Hasegawa | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1124 days.

Signed and Sealed this
Fifteenth Day of February, 2011

David J. Kappos
*Director of the United States Patent and Trademark Office*